United States Patent [19]

Meier et al.

[11] Patent Number: 4,749,709
[45] Date of Patent: Jun. 7, 1988

[54] METHOD OF INHIBITING BODY FAT STORES

[75] Inventors: Albert H. Meier; Anthony H. Cincotta, both of Baton Rouge, La.

[73] Assignee: Louisiana State University and Agricultural and Mechanical College, Baton Rouge, La.

[21] Appl. No.: 40,188

[22] Filed: Apr. 17, 1987

Related U.S. Application Data

[63] Continuation-in-part of Ser. No. 837,148, Apr. 7, 1986, Pat. No. 4,659,715.

[51] Int. Cl.$^4$ ............................................. A61K 31/44
[52] U.S. Cl. ................................................... 514/288
[58] Field of Search ....................................... 514/288

*Primary Examiner*—Stanley J. Friedman
*Attorney, Agent, or Firm*—Edgar E. Spielman, Jr.; James M. Pelton

[57] ABSTRACT

A method for reducing body fat stores in vertebrate animals by administering a prolactin-inhibitor to the animal in a dose which effects such reduction without a concomitant decrease in body weight is disclosed.

7 Claims, No Drawings

METHOD OF INHIBITING BODY FAT STORES

CROSS-REFERENCE TO A RELATED APPLICATION

This application is a continuation-in-part of our copending application, Ser. No. 837,148, filed Apr. 7, 1986, now U.S. Pat. No. 4,659,715, issued Apr. 21, 1987.

BACKGROUND OF THE INVENTION

This invention relates to a method for reducing body fat stores in vertebrate animals without causing significant weight loss by administering to the animal an agent to suppress its prolactin secretion.

A method for reducing body fat stores without causing significant weight loss would be valuable to the livestock industry as a better grade of meat could be obtained without a concomitant lowering of the price paid per animal due to weight loss. In humans, such a method would be valuable to athletes who strive to obtain a low percentage of body fat without a loss in muscle mass.

It is, therefore, an object of this invention to provide this method.

THE INVENTION

In accordance with the method of this invention, it has been found that inhibiting the pituitary gland's production of prolactin will result in body fat stores being reduced in vertebrate animals without significant body weight loss.

Inhibiting prolactin secretion is effected by administering, to the animal, a pharmaceutically appropriate dose of a prolactin-inhibitor, such as various ergot-related compounds. The dosing may be by oral or by peritoneal, e.g., subcutaneous or intramuscular injection, administration.

Exemplary of ergot-related prolactin-inhibitors are: 2-bromo-$\alpha$-ergocryptine; 6-methyl-8$\beta$-carbobenzyloxy-aminomethyl-10$\alpha$-ergoline; 1,6-dimethyl-8$\beta$-carbobenzyloxy-aminomethyl-10$\alpha$-ergoline; 8-acylaminoergolenes, such as 6-methyl-8$\alpha$-(N-acyl)amino-9-ergolene and 6-methyl-8$\alpha$-(N-phenylacetyl)amino-9-ergolene; ergocornine; 9,10-dihydroergocornine; and D-2-halo-6-alkyl-8-substituted ergolines, e.g., D-2-bromo-6-methyl-8-cyanomethylergoline. The foregoing ergot-related compounds and the processes for their formation are known to the art. From the standpoint of side effects, especially that on fertility, 2-bromo-$\alpha$-ergocryptine has been found to be highly suitable for the method of this invention.

The non-toxic salts of the prolactin-inhibiting ergot-related compounds formed from pharmaceutically acceptable acids are also useful in the method of this invention.

Different animal species exhibit dissimilar prolactin-inhibition sensitivity to ergot-related compounds. Hence, the dosage required to obtain significant reductions in body fat stores varies over a fairly wide range. In fact, it has been found that a proper dosage range for a selected animal species also can be quite wide. For example, a study of golden hamsters showed that an intraperitoneal daily dose, as low as 0.15 mg/kg body weight and as high as 6.00 mg/kg of body weight, of 2-bromo-$\alpha$-ergocryptine in divided doses of two times a day for a 24-day period gave good reductions in body fat stores without significant losses in body weight. Thus, the suitable dosage range is best determined empirically for each animal species. Generally, the minimum dosage to obtain the body fat stores reduction sought will be the preferred dosage as the chance of unwanted side effects is diminished and the cost of dosing will be kept to a minimum. As a guide, most animal species upon which the method of this invention would be used commercially, e.g., swine, ruminants and humans, will exhibit the body fat store reduction desired with daily intramuscular dosages of 2-bromo-$\alpha$-ergocryptine within the range of from about 0.15 mg/kg body weight to about 6.0 mg/kg body weight.

Capsules or tablets containing the unit doses of the ergot-related compound are suitable for oral dosing. Generally, the ergot-related compound will be used as a pharmaceutically acceptable salt when administered orally. If peritoneal dosing is used, the ergot-related compound will be provided with conventional sterile diluents, such as, mannitol, sucrose, vegetable oil, etc. The duration of administration may vary from species to species.

The period of time over which the dosage of the prolactin-inhibitor is administered is an important aspect of the method of this invention. However, generally, if the animal is for commercial slaughtering, the period of time for dosage should be at least 7 days in length and up to the fifth day before slaughter. It is believed desirable to cease dosing five days before slaughter to allow the prolactin-inhibitor to be substantially eliminated from the animal's system at the time of slaughter. If the animal is being subjected to long-term treatment, in accordance with the method of this invention, then the dosing is first given at the above levels for that period of time necessary to achieve the desired body fat stores level and is thereafter dosed so as to maintain that level for the extended period. In either case, for the dosing to yield significant results, the dosing should be maintained for at least 7 days and preferably at least about 10 days.

It is theorized, though the method of this invention is not limited thereby, that the administration of a prolactin-inhibitor to an animal reduces or abolishes the lipogenic responses of hepatocytes to insulin and severely depresses the hepatocyte insulin receptor number. Since body fat stores are dependent on the synergistic action between prolactin and insulin to increase hepatic lipogenesis, the abolishment of prolactin secretion stills hepatic lipogenesis.

EXAMPLES

Mature (3-7 months old) male golden hamsters, *Mesocricetus auratus* (body weight: 100-150 g) were caged in pairs, fed ad libitum, maintained at 23° C. and provided 14-h daily photoperiods (light onset: 0800 h). The hamsters were injected (i.p.) daily at 0800 and 1400 with 2-bromo-$\alpha$-ergocryptine (300 ug/0.1 ml peanut oil) or peanut oil (controls). Food consumption was monitored daily. After 24 days of treatment, the animals were killed by overdose of sodium pentobarbital to obtain body weights, abdominal and epididymal fat pad weights, and testes and seminal vescicle weights. Statistical differences between the two groups were tested by Student's t to determine the significance, "P". The results are given in the table.

In the Examples shown in Table I the 2-bromo-$\alpha$-ergocryptine treatment reduced (P<0.01) abdominal fat weight 47% and epididymal fat weight 32% compared with control treatment. However, 2-bromo-$\alpha$- ergocryptine did not alter body weight, food consumption, paired testes weights or seminal vescicle weights. The constancy of testes and seminal vescicle weights is good indication that the 2-bromo-α-ergocryptine treatment of this invention has no effect on the animals' fertility.

Since body weight was not adversely affected by treatment with 2-bromo-α-ergocryptine, it is apparent that the method of this invention causes the animal to direct metabolic energy away from lipogenesis and towards protein formation.

For the Examples shown in Table II, the treatment was for 10 days using the same dosage and prolactin-inhibitor as was used for the Examples of Table I. The animals had an initial average body weight of 100 g.

effective dosage of an ergot-related prolactin-inhibiting compound for a period of at least 7 days and until a predetermined amount of said body fat stores is reduced.

2. The method of claim 1 wherein said ergot-related prolactin inhibiting compound is 2-bromo-α-ergocryptine or its salts formed from pharmaceutically acceptable acids.

3. The method of claim 1 wherein said dosage is administered over a period of at least 10 days.

4. The method of claim 1 wherein said vertebrate animal in need is of a species which is for comercial slaughter and wherein said method additionally comprises ceasing said dosage at least 5 days before slaughtering of said vertebrate animal.

TABLE I

| TREATMENT | N | BODY WT. (% INCR.) | INDICES OF BODY FAT STORES | | | |
|---|---|---|---|---|---|---|
| | | | EPIDIDYMAL FAT PAD | | ABDOMINAL FAT PAD | |
| | | | (g) | (% B.W.) | (g) | (% B.W.) |
| Experiment 1 - (3-4 months of age) | | | | | | |
| Control | 9 | 11.5 ± 4.0 | 1.73 ± 0.06 | 1.37 ± 0.05 | 0.84 ± 0.03 | 0.67 ± 0.03 |
| 2-Bromo-α-ergocryptine (6.00 mg/kg/day) | 10 | 16.3 ± 2.4 | 1.17 ± 0.07[1] | 0.93 ± 0.05[1] | 0.43 ± 0.02[1] | 0.38 ± 0.01[1] |
| Experiment 2 - (7 months of age) | | | | | | |
| Control | 8 | 3.3 ± 0.9 | 1.35 ± 0.07 | 1.10 ± 0.05 | 0.96 ± 0.08 | 0.77 ± 0.06 |
| 2-Bromo-α-ergocryptine (6.00 mg/kg/day) | 8 | 5.4 ± 1.2 | 1.07 ± 0.09[2] | 0.76 ± 0.04[1] | 0.72 ± 0.07[2] | 0.54 ± 0.04[1] |
| 2-Bromo-α-ergocryptine (2.00 mg/kg/day) | 7 | 3.0 ± 1.1 | 1.08 ± 0.05[1] | 0.90 ± 0.05[1] | 0.75 ± 0.08[3] | 0.63 ± 0.08[3] |
| 2-Bromo-α-ergocryptine (.15 mg/kg/day) | 8 | 1.6 ± 1.2 | 0.91 ± 0.06[1] | 0.86 ± 0.05[1] | 0.60 ± 0.04[1] | 0.56 ± 0.04[1] |

| TREATMENT | LIVER WT. (g) | FOOD CONSUMED (g/day/animal) | REPRODUCTIVE INDICES | | |
|---|---|---|---|---|---|
| | | | TESTES (g) | SEMINAL VESTICLES (g) | ACCESSORY SEX ORGAN (g) |
| Experiment 1 - (3-4 months of age) | | | | | |
| Control | 5.2 ± 0.2 | 8.8 ± 0.2 | 4.0 ± 0.1 | 1.62 ± 0.08 | 0.98 ± 0.10 |
| 2-Bromo-α-ergocryptine (6.00 mg/kg/day) | 5.3 ± 0.3 | 8.8 ± 0.2 | 3.9 ± 0.1 | 1.68 ± 0.10 | 0.90 ± 0.10 |
| Experiment 2 - (7 months of age) | | | | | |
| Control | 4.9 ± 0.5 | 10.4 ± 0.3 | 3.5 ± 0.2 | 1.42 ± 0.05 | 0.84 ± 0.05 |
| 2-Bromo-α-ergocryptine (6.00 mg/kg/day) | 5.6 ± 0.7 | 11.2 ± 0.3 | 3.6 ± 0.2 | 1.53 ± 0.06 | 0.78 ± 0.05 |
| 2-Bromo-α-ergocryptine (2.00 mg/kg/day) | 5.0 ± 0.3 | 9.8 ± 0.3 | 3.3 ± 0.2 | 1.57 ± 0.03 | 0.79 ± 0.05 |
| 2-Bromo-α-ergocryptine (.15 mg/kg/day) | 4.5 ± 0.2 | 9.2 ± 0.5 | 3.3 ± 0.1 | 1.40 ± 0.07 | 0.76 ± 0.06 |

[1] Significantly less than control (P less than 0.01)
[2] Significantly less than control (P less than 0.05)
[3] Not significantly different from control
[4] Number of Hamsters

TABLE II

| TREATMENT | N | FINAL BODY WT. | INDICES OF BODY FAT STORES | | | | LIVER WT. (g) | FOOD CONSUMED (g/day/animal) |
|---|---|---|---|---|---|---|---|---|
| | | | EPIDIDYMAL FAT PAD | | ABDOMINAL FAT PAD | | | |
| | | | (g) | (% B.W.) | (g) | (% B.W.) | | |
| Experiment 1 - (3-4 months of age) | | | | | | | | |
| Control | 5 | 116 ± 12 | 1.23 ± 0.08 | | 0.88 ± 0.08 | | 4.5 ± 0.2 | |
| 2-Bromo-α-ergocryptine (6.00 mg/kg/day) | 5 | 109 ± 7 | 0.85 ± 0.14[1] | | 0.42 ± 0.06[1] | | 4.3 ± 0.3 | |
| Experiment 2 - (7 months of age) | | | | | | | | |
| Control | 5 | 103 ± 6 | 1.50 ± 0.18 | 1.43 ± 0.11 | 1.17 ± 0.22 | 1.10 ± 0.16 | | 8.6 |
| 2-Bromo-α-ergocryptine (6.00 mg/kg/day) | 5 | 91 ± 3 | 0.98 ± 0.05[1] | 1.07 ± 0.04[1] | 0.46 ± 0.05[1] | 0.50 ± 0.05[1] | | 8.5 |

[1] Significantly less than control (P less than 0.05)
N Number of hamsters

We claim:

1. A method for treating a vertebrate animal to reduce its body fat stores without substantial concomitant loss in its body weight, which method comprises administering to said animal in need of such treatment an 5. The method of claim 4 wherein said dosage is maintained for about 10 days.

6. The method of claim 1 wherein said vertebrate animal in need is a swine or a ruminant, said ergot-related prolactin inhibiting compound is 2-bromo-α-ergocryptine and said dosage, on a daily basis, is within the range of from about 0.15 mg/kg body weight to about 6.0 mg/kg body weight.

7. The method of claim 6 wherein said dosage is maintained for about 10 days.

* * * * *

UNITED STATES PATENT AND TRADEMARK OFFICE
CERTIFICATE OF CORRECTION

PATENT NO. : 4,749,709
DATED : June 7, 1988
INVENTOR(S) : Albert H. MEIER et al.

It is certified that error appears in the above-indentified patent and that said Letters Patent is hereby corrected as shown below:

Title page, item [63], Related U.S. Application Data, change "Apr." to --Mar.--.
Col. 1, line 7, change "Apr." to --Mar.--.

Signed and Sealed this

Second Day of September, 1997

Attest:

BRUCE LEHMAN

Attesting Officer

Commissioner of Patents and Trademarks